United States Patent
Bertin (10) Patent No.: US 9,796,657 B2
(45) Date of Patent: Oct. 24, 2017

(54) POLYOL ESTERS OF METATHESIZED FATTY ACIDS AND USES THEREOF

(71) Applicant: Elevance Renewable Sciences, Inc., Woodridge, IL (US)

(72) Inventor: Paul A. Bertin, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 15/075,734

(22) Filed: Mar. 21, 2016

(65) Prior Publication Data
US 2016/0304434 A1   Oct. 20, 2016

Related U.S. Application Data

(60) Provisional application No. 62/137,685, filed on Mar. 24, 2015, provisional application No. 62/236,034, filed on Oct. 1, 2015.

(51) Int. Cl.
| | | |
|---|---|---|
| C07C 69/533 | (2006.01) | |
| C09D 7/12 | (2006.01) | |
| C07C 69/587 | (2006.01) | |
| C09D 107/02 | (2006.01) | |
| C09D 121/02 | (2006.01) | |
| C11D 3/20 | (2006.01) | |

(52) U.S. Cl.
CPC .......... *C07C 69/533* (2013.01); *C07C 69/587* (2013.01); *C09D 7/12* (2013.01); *C09D 7/1233* (2013.01); *C09D 107/02* (2013.01); *C09D 121/02* (2013.01); *C11D 3/20* (2013.01); *C11D 3/2093* (2013.01)

(58) Field of Classification Search
None
See application file for complete search history.

(56) References Cited

U.S. PATENT DOCUMENTS

| 4,545,941 A | 10/1985 | Rosenburg | |
|---|---|---|---|
| 2009/0311403 A1* | 12/2009 | Grab | A21D 13/08 426/535 |
| 2013/0288946 A1* | 10/2013 | Allen | A01N 25/04 510/416 |
| 2014/0005423 A1* | 1/2014 | Allen | C07C 67/26 554/85 |
| 2014/0171677 A1* | 6/2014 | Bertin | C07C 5/25 560/205 |

FOREIGN PATENT DOCUMENTS

| EP | 0355842 | * 2/1990 | ............. A61K 7/42 |
|---|---|---|---|
| WO | WO 2013/162924 | * 10/2013 | ............. C11D 1/65 |
| WO | 2014/058867 | 4/2014 | |
| WO | WO 2014/058867 | * 4/2014 | ........... C07C 67/475 |

OTHER PUBLICATIONS

Int'l Search Report & Written Opinion of Int'l Searching Authority, PCT App. No. PCT/US2016/023383, dated Jun. 27, 2016.

* cited by examiner

*Primary Examiner* — Yate K Cutliff
(74) *Attorney, Agent, or Firm* — Kilpatrick Townsend & Stockton LLP (57) ABSTRACT

Polyol esters of metathesized fatty acids are generally disclosed herein. Methods of using such compounds, for example, as cleaning agents, solvents, and coalescents for paints and coatings, are also disclosed.

15 Claims, 1 Drawing Sheet

POLYOL ESTERS OF METATHESIZED FATTY ACIDS AND USES THEREOF

CROSS-REFERENCE TO RELATED APPLICATIONS

The present application claims the benefit of priority of U.S. Provisional Application No. 62/137,685, filed Mar. 24, 2015; and 62/236,034, filed Oct. 1, 2015; both of which are hereby incorporated by reference in their entirety.

TECHNICAL FIELD

Polyol esters of metathesized fatty acids are generally disclosed herein. Methods of using such compounds, for example, as cleaning agents, solvents, and coalescents for paints and coatings, are also disclosed.

BACKGROUND

Natural oils, such as seed oils, and their derivatives can provide useful starting materials for making a variety of chemical compounds. Because such compounds contain a certain degree of inherent functionality that is otherwise absent from petroleum-sourced materials, it can often be more desirable, if not cheaper, to use natural oils or their derivatives as a starting point for making certain compounds. Additionally, natural oils and their derivatives are generally sourced from renewable feedstocks. Thus, by using such starting materials, one can enjoy the concomitant advantage of developing useful chemical products without consuming limited supplies of petroleum. Further, refining natural oils can be less intensive in terms of the severity of the conditions required to carry out the refining process.

Natural oils can be refined in a variety of ways. For example, processes that rely on microorganisms can be used, such as fermentation. Chemical processes can also be used. For example, when the natural oils contain at least one carbon-carbon double bond, olefin metathesis can provide a useful means of refining a natural oil and making useful chemicals from the compounds in the feedstock.

Metathesis is a catalytic reaction that involves the interchange of alkylidene units among compounds containing one or more double bonds (e.g., olefinic compounds) via the cleavage and formation of carbon-carbon double bonds. Metathesis may occur between two like molecules (often referred to as "self-metathesis") or it may occur between two different molecules (often referred to as "cross-metathesis"). Self-metathesis may be represented schematically as shown below in Equation (A):

(A)

wherein $R^a$ and $R^b$ are organic groups.

Cross-metathesis may be represented schematically as shown below in Equation (B):

(B)

wherein $R^a$, $R^b$, $R^c$, and $R^d$ are organic groups. Self-metathesis will also generally occur concurrently with cross-metathesis.

In recent years, there has been an increased demand for environmentally friendly techniques for manufacturing materials typically derived from petroleum sources, which can be made by processes that involve olefin metathesis. This has led to studies of the feasibility of manufacturing biofuels, waxes, plastics, and the like, using natural oil feedstocks, such as vegetable and/or seed-based oils.

Natural oil feedstocks of interest include, but are not limited to, oils such as natural oils (e.g., vegetable oils, fish oils, algae oils, and animal fats), and derivatives of natural oils, such as free fatty acids and fatty acid alkyl (e.g., methyl) esters. These natural oil feedstocks may be converted into industrially useful chemicals (e.g., waxes, plastics, cosmetics, biofuels, etc.) by any number of different metathesis reactions. Significant reaction classes include, as non-limiting examples, self-metathesis, cross-metathesis with olefins, and ring-opening metathesis reactions. Non-limiting examples of useful metathesis catalysts are described in further detail below.

Refining processes for natural oils (e.g., employing metathesis) can lead to compounds having chain lengths closer to those generally desired for chemical intermediates of specialty chemicals (e.g., about 9 to 15 carbon atoms). By using these compounds as starting materials, it is possible to create a variety of novel chemical compounds that may be used for a variety of useful purposes. Further, because these compounds contain somewhat different chemical functionality than similar molecular-weight compounds derived in other ways, metathesis-derived variants may have beneficial properties that could not have been appreciated otherwise.

Meanwhile, the use of certain industrial solvents has curtailed in recent years due, in part, to concerns over their impact on the environment and their effects on general health and safety. This is especially true of solvents known to have a high volatile organic content (VOC), as such compounds may contribute to greenhouse gas production and ozone depletion. In some instances, traditional high VOC solvents can also be carcinogenic, teratogenic, toxic, and/or mutagenic. Therefore, a number of common solvents have come under increased regulatory scrutiny and therefore suffer from decreased use. Such solvents include aromatics (e.g., benzene, toluene, xylenes, and the like), ketones (e.g., methyl ethyl ketone, methyl isobutyl ketone, and the like), halogenated organics (e.g., dichloromethane, perchloroethylene, and the like), glycol ethers, and alcohols (e.g., methanol, isopropanol, ethylene glycol, and the like).

Certain derivatives of renewable feedstocks can provide more suitable alternatives to high VOC solvents. For example, fatty acid alkyl esters (e.g., from the transesterification of vegetable oils, animal fats, or other lipids) can provide environmentally friendly alternatives to traditional oxygenated solvents. Methyl soyate, for example, has a low VOC value, a high flash point, a low toxicity, and a high biodegradability. Terpene oils from citrus and pine (d-limonene and pinene, respectively) may also serve as suitable alternatives to certain traditional organic solvents.

Such renewable solvents are not without their problems, however. For example, d-limonene and dipentene (a racemate of d-limonene) are both acute and chronic aquatic toxins, and also have an irritating and sensitizing effect on the skin. Further, d-limonene is highly inflammable (e.g., more so than petroleum distillates) and can be subject to fluctuations in supply and price. Fatty acid alkyl esters can overcome some of these deficiencies of terpene oils, but can also exhibit poor solvency relative to certain incumbents.

Thus, there is a continuing need to develop solvent compounds and compositions that are renewably sourced, exhibit high solvency, and have a desirable health and safety profile (e.g., in terms of toxicity and VOCs).

SUMMARY

In a first aspect, the disclosure provides compounds derived from the metathesis of a natural oil that provide low VOCs and that function effectively in many solvent-related applications.

In a second aspect, the disclosure provides a compound of formula (I):

(I)

wherein:

$R^1$ is —H, —CH$_2$—CH$_3$, —CH$_2$—CH=CH$_2$, or —CH$_2$—CH=CH—CH$_2$—CH$_3$; and $R^2$ is a polyol residue, such as a residue of ethylene glycol, propylene glycol, and the like.

In a third aspect, the disclosure provides a compound of formula (II):

(II)

wherein:

$R^{1'}$ is —H, —CH$_2$—CH$_3$, —CH$_2$—CH=CH$_2$, or —CH$_2$—CH=CH—CH$_2$—CH$_3$; and $R^{2'}$ is a alkoxylate residue, such as a residue of diethylene glycol, dipropylene glycol, and the like.

In a fourth aspect, the disclosure provides cleaning compositions that include one or more compounds of the second or third aspects. In some embodiments thereof, the cleaning composition includes a carrier, and, optionally, a surfactant.

In a fifth aspect, the disclosure provides petroleum compositions that include one or more compounds of the second or third aspects and a petroleum fluid.

In a sixth aspect, the disclosure provides paint or coating compositions that include water, a film-forming polymer, and one or more compounds of the second or third aspects.

In a seventh aspect, the disclosure provides methods for painting or coating a surface, comprising disposing a composition of the sixth aspect on the surface.

Further aspects and embodiments are provided in the foregoing drawings, detailed description and claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

The FIGURE shows a non-limiting example of a compound made according to certain embodiments disclosed herein, wherein: $R^1$ is —H, —CH$_2$—CH$_3$, —CH$_2$—CH=CH$_2$, or —CH$_2$—CH=CH—CH$_2$—CH$_3$; and $R^2$ is a polyol residue, such as a residue of ethylene glycol, 1,2-propylene glycol, 1,3-propylene glycol, and the like.

DETAILED DESCRIPTION

Figure 1:
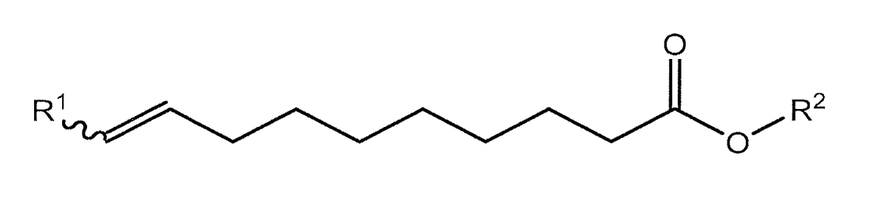

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin," while an olefin having a non-terminal carbon-carbon double bond can be referred to as an "internal olefin."

As used herein, the term "low-molecular-weight olefin" may refer to any one or combination of unsaturated straight, branched, or cyclic hydrocarbons in the $C_{2-14}$ range. Low-molecular-weight olefins include "alpha-olefins" or "terminal olefins," wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. In one embodiment, it may be preferable to use a mixture of linear and branched $C_4$ olefins (i.e., combinations of: 1-butene, 2-butene, and/or isobutene). In other embodiments, a higher range of $C_{11-14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "alpha-olefin" refers to an olefin (as defined above) that has a terminal carbon-carbon double bond. In some embodiments, the alpha-olefin is a terminal alkene, which is an alkene (as defined above) having a terminal carbon-carbon double bond. Additional carbon-carbon double bonds can be present.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified.

It is noted that an olefin may also comprise an ester, and an ester may also comprise an olefin, if the R or R' group in the general formula R—COO—R' contains an unsaturated carbon-carbon double bond. Such compounds can be referred to as "unsaturated esters" or "olefin esters." Further, a "terminal olefin ester" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Polyol Esters of Unsaturated Fatty Acids

In certain aspects, the disclosure provides polyol esters of unsaturated fatty acids. In some embodiments, the polyol esters of unsaturated fatty acids are compounds of formula (I):

(I)

wherein: $R^1$ is —H, —$CH_2$—$CH_3$, —$CH_2$—$CH$=$CH_2$, or —$CH_2$—$CH$=$CH$—$CH_2$—$CH_3$; and $R^2$ is selected from the group consisting of: —$CH_2$—$CH_2$—OH, —$CH_2$—$CH_2$—O—$R^3$, —$CH_2$—$CH(OH)$—$CH_3$, —$CH_2$—$CH(O$—$R^4)$—$CH_3$, —$CH(-CH_3)$—$CH_2$—OH, —$CH(-CH_3)$—$CH_2$—$OR^5$, —$CH_2$—$CH_2$—$CH_2$—OH, —$CH_2$—$CH_2$—$CH_2$—O—$R^6$, —$CH_2$—$CH_2$—$CH_2$—$CH_2$—OH, —$CH_2$—$CH_2$—$CH_2$—$CH_2$—O—$R^7$, —$CH_2$—$CH(-CH_3)$—$CH_2$—OH, —$CH_2$—$CH(-CH_3)$—$CH_2$—$OR^8$, —$CH_2$—$C(-CH_3)_2$—$CH_2$—OH, —$CH_2$—$C(-CH_3)_2$—$CH_2$—$OR^9$, —$CH_2$—$CH_2$—$CH(-CH_3)$—$CH_2$—$CH_2$—OH, —$CH_2$—$CH(-CH_3)$—$CH_2$—$CH_2$—$OR^{10}$, —$CH_2$—$CH(-OH)$—$CH_2$—OH, —$CH_2$—$CH(-OH)$—$CH_2$—$OR^{11}$, —$CH_2$—$CH(-OR^{12})$—$CH_2$—OH, —$CH_2$—$CH(-OR^{12})$—$CH_2$—$OR^{11}$, —$CH(-CH_2$—OH)($-CH_2$—OH), —$CH(-CH_2$—$OR^{13})(-CH_2$—OH), —$CH(-CH_2$—OH)($-CH_2$—$OR^{14}$), —$CH(-CH_2$—$OR^{13})(-CH_2$—$OR^{14}$); and $R^3$, $R^4$, $R^5$, $R^6$, $R^7$, $R^8$, $R^9$, $R^{10}$, $R^{11}$, $R^{12}$, $R^{13}$, and $R^{14}$ are independently methyl or ethyl.

In some embodiments, $R^1$ is —H. In some embodiments, $R^1$ is —$CH_2$—$CH_3$, —$CH_2$—$CH$=$CH_2$, or —$CH_2$—$CH$=$CH$—$CH_2$—$CH_3$. In some embodiments, $R^1$ is —$CH_2$—$CH_3$. In some embodiments, $R^1$ is —$CH_2$—$CH$=$CH_2$. In some embodiments, $R^1$ is —$CH_2$—$CH$=$CH$—$CH_2$—$CH_3$.

In some embodiments of any of the aforementioned embodiments, $R^2$ is —$CH_2$—$CH_2$—OH. In some embodiments of any of the aforementioned embodiments, $R^2$ is —$CH_2$—$CH_2$—O—$R^3$. In some such embodiments, $R^3$ is methyl. In some such embodiments, $R^3$ is ethyl.

In some embodiments of any of the aforementioned embodiments, $R^2$ is —$CH_2$—$CH(OH)$—$CH_3$. In some embodiments of any of the aforementioned embodiments, $R^2$ is —$CH_2$—$CH(O$—$R^4)$—$CH_3$. In some such embodiments, $R^4$ is methyl. In some such embodiments, $R^4$ is ethyl.

In some embodiments of any of the aforementioned embodiments, $R^2$ is —$CH(-CH_3)$—$CH_2$—OH. In some embodiments of any of the aforementioned embodiments, $R^2$ is —$CH(-CH_3)$—$CH_2$—$OR^5$. In some such embodiments, $R^5$ is methyl. In some such embodiments, $R^5$ is ethyl.

In some embodiments of any of the aforementioned embodiments, $R^2$ is —$CH_2$—$CH_2$—$CH_2$—OH. In some embodiments of any of the aforementioned embodiments, $R^2$ is —$CH_2$—$CH_2$—$CH_2$—O—$R^6$. In some such embodiments, $R^6$ is methyl. In some such embodiments, $R^6$ is ethyl.

In some embodiments of any of the aforementioned embodiments, $R^2$ is —$CH_2$—$CH_2$—$CH_2$—$CH_2$—OH. In some embodiments of any of the aforementioned embodiments, $R^2$ is —$CH_2$—$CH_2$—$CH_2$—$CH_2$—O—$R^7$. In some such embodiments, $R^7$ is methyl. In some such embodiments, $R^7$ is ethyl.

In some embodiments of any of the aforementioned embodiments, $R^2$ is —$CH_2$—$CH(-CH_3)$—$CH_2$—OH. In some embodiments of any of the aforementioned embodiments, $R^2$ is —$CH_2$—$CH(-CH_3)$—$CH_2$—$OR^8$. In some embodiments, $R^8$ is methyl. In some embodiments, $R^8$ is ethyl.

In some embodiments of any of the aforementioned embodiments, $R^2$ is —$CH_2$—$C(-CH_3)_2$—$CH_2$—OH. In some embodiments of any of the aforementioned embodiments, $R^2$ is —$CH_2$—$C(-CH_3)_2$—$CH_2$—$OR^9$. In some such embodiments, $R^9$ is methyl. In some such embodiments, $R^9$ is ethyl.

In some embodiments of any of the aforementioned embodiments, $R^2$ is —$CH_2$—$CH_2$—$CH(-CH_3)$—$CH_2$—OH. In some embodiments of any of the aforementioned embodiments, $R^2$ is —$CH_2$—$CH_2$—$CH(-CH_3)$—$CH_2$—$CH_2$—$OR^{10}$. In some such embodiments, $R^{10}$ is methyl. In some such embodiments, $R^{10}$ is ethyl.

In some embodiments of any of the aforementioned embodiments, $R^2$ is —$CH_2$—CH(—OH)—$CH_2$—OH. In some embodiments of any of the aforementioned embodiments, $R^2$ is —$CH_2$—CH(—OH)—$CH_2$—$OR^{11}$. In some such embodiments, $R^{11}$ is methyl. In some such embodiments, $R^{11}$ is ethyl. In some embodiments of any of the aforementioned embodiments, $R^2$ is —$CH_2$—CH(—$OR^{12}$)—$CH_2$—OH. In some such embodiments, $R^{12}$ is methyl. In some such embodiments, $R^{12}$ is ethyl. In some embodiments of any of the aforementioned embodiments, $R^2$ is —$CH_2$—CH(—$OR^{12}$)—$CH_2$—$OR^{11}$. In some such embodiments, $R^{11}$ is methyl. In some such embodiments, $R^{11}$ is ethyl. In some such embodiments, $R^{12}$ is methyl. In some such embodiments, $R^{12}$ is ethyl.

In some embodiments of any of the aforementioned embodiments, $R^2$ is —CH(—$CH_2$—OH)(—$CH_2$—OH). In some embodiments of any of the aforementioned embodiments, $R^2$ is —CH(—$CH_2$—$OR^{13}$)(—$CH_2$—OH). In some such embodiments, $R^{13}$ is methyl. In some such embodiments, $R^{13}$ is ethyl. In some embodiments of any of the aforementioned embodiments, $R^2$ is —CH(—$CH_2$—OH)(—$CH_2$—$OR^{14}$). In some such embodiments, $R^{14}$ is methyl. In some such embodiments, $R^{14}$ is ethyl. In some embodiments of any of the aforementioned embodiments, $R^2$ is —CH(—$CH_2$—$OR^{13}$)(—$CH_2$—$OR^{14}$). In some such embodiments, $R^{13}$ is methyl. In some such embodiments, $R^{13}$ is ethyl. In some such embodiments, $R^{14}$ is methyl. In some such embodiments, $R^{14}$ is ethyl.

In certain aspects, the disclosure provides polyol esters of unsaturated fatty acids. In some embodiments, the polyol esters of unsaturated fatty acids are compounds of formula (I):

(II)

wherein: $R^{1'}$ is —H, —$CH_2$—$CH_3$, —$CH_2$—CH=$CH_2$, or —$CH_2$—CH=CH—$CH_2$—$CH_3$; and $R^{2'}$ is selected from the group consisting of: $R^{2'}$ is selected from the group consisting of: —$CH_2$—$CH_2$(—O—$CH_2$—$CH_2$)$_w$—OH, —$CH_2$—$CH_2$(—O—$CH_2$—$CH_2$)$_x$—O—$R^{15}$; —$CH_2$—CH(—$CH_3$)(—O—$CH_2$—CH(—$CH_3$))$_y$—OH, and —$CH_2$—CH(—$CH_3$)(—O—$CH_2$—CH(—$CH_3$))$_z$—O—$R^{16}$; $R^{15}$ and $R^{16}$ are independently methyl or ethyl; and w, x, y, and z are independently 1, 2, or 3.

In some embodiments, $R^{1'}$ is —H. In some embodiments, $R^{1'}$ is —$CH_2$—$CH_3$, —$CH_2$—CH=$CH_2$, or —$CH_2$—CH=CH—$CH_2$—$CH_3$. In some embodiments, $R^{1'}$ is —$CH_2$—$CH_3$. In some embodiments, $R^{1'}$ is —$CH_2$—CH=$CH_2$. In some embodiments, $R^{1'}$ is —$CH_2$—CH=CH—$CH_2$—$CH_3$.

In some embodiments of any of the aforementioned embodiments, $R^{2'}$ is —$CH_2$—$CH_2$(—O—$CH_2$—$CH_2$)$_w$—OH. In some such embodiments, w is 1 or 2. In some embodiments, w is 1, and in others w is 2. In some embodiments of any of the aforementioned embodiments, $R^{2'}$ is —$CH_2$—$CH_2$(—O—$CH_2$—$CH_2$)$_x$—O—$R^{15}$. In some such embodiments, $R^{15}$ is methyl. In some such embodiments, $R^{15}$ is ethyl. In some such embodiments, x is 1 or 2. In some embodiments, x is 1 or 2. In some embodiments, x is 1, and in others, x is 2.

In some embodiments of any of the aforementioned embodiments, $R^{2'}$ is —$CH_2$—CH(—$CH_3$)(—O—$CH_2$—CH(—$CH_3$))$_y$—OH. In some such embodiments, y is 1 or 2. In some such embodiments, y is 1 or 2. In some embodiments, y is 1, and, in others, y is 2. In some embodiments of any of the aforementioned embodiments, $R^{2'}$ is —$CH_2$—CH(—$CH_3$)(—O—$CH_2$—CH(—$CH_3$))$_z$—O—$R^{16}$. In some such embodiments, $R^{16}$ is methyl. In some such embodiments, $R^{16}$ is ethyl. In some such embodiments, z is 1 or 2. In some embodiments, z is 1 or 2. In some embodiments z is 1, and, in others, z is 2.

Cleaning Compositions

In certain aspects, the disclosure provides compositions that include a polyol ester of an unsaturated fatty acid (according to any of the above embodiments), e.g., as a cleaning agent.

In some embodiments, the composition consists of or consists essentially of the polyol ester of an unsaturated fatty acid. In some other embodiments, however, the composition includes water. In some such embodiments, the composition further includes a surfactant, such as a non-ionic surfactant, an anionic surfactants, a cationic surfactant, or combinations thereof. In some embodiments, the composition is an emulsion, such as a micro-emulsion. In some such embodiments, the emulsion is an oil-in-water emulsion. In some other embodiments, the emulsion is a water-in-oil emulsion.

The cleaning agents disclosed above can be used in various cleaning applications, including, but not limited to, degreasing, such as industrial degreasing, cleaning textiles or other woven fibers, such as in laundry-related applications (e.g., pre-treatment or detergent), cleaning food or food residues, or cleaning oilfield-related equipment, such as cleaning materials containing paraffins, asphaltenes, and the like.

Petroleum Compositions

In certain aspects, the disclosure provides petroleum compositions that include a petroleum fluid and a polyol ester of an unsaturated fatty acid (according to any of the above embodiments), e.g., as an agent for improving the pour point by dissolving paraffins and/or asphaltenes. In some embodiments, the petroleum fluid is crude oil.

Coating or Paint Compositions Including a Coalescing Aid

In certain aspects, the disclosure provides compositions that include an aqueous carrier, a film-forming polymer, and a polyol ester of an unsaturated fatty acid (according to any of the above embodiments), e.g., as a coalescing aid.

The compositions comprise an aqueous carrier and a film-forming polymer. Any suitable aqueous carrier can be used. In general, water is the predominant component of the aqueous carrier, although amounts of additional ingredients can be dissolved in the water. Such additional ingredients include, but are not limited to, surfactants, thickeners, rheology modifiers, pigments or other colorants, defoamers, co-solvents, and the like. Suitable co-solvents include solvents that are miscible with water. In some embodiments, one or more of these additional ingredients may, in addition to being dissolved in the aqueous medium, be suspended in the aqueous medium (e.g., as part of an emulsion). In some embodiments, the aqueous medium comprises at least 70% by weight, or at least 80% by weight, or at least 90% by weight, or at least 95% by weight, or at least 97% by weight, water.

In some embodiments, it may be desirable to adjust the pH of the aqueous medium, depending, for example, on whether one or more components in the composition may perform better for certain end uses. In some embodiments, the aqueous medium is approximately neutral, meaning that it has a pH of 6 to 8. In some other embodiments, the aqueous medium is an acidic medium, such as, for example, a medium having a pH less than 7. In some such embodiments, the pH is in the range of 3 to 7 (but not including 7), or 4 to 6. In some other embodiments, the aqueous medium is alkaline, such as, for example, a medium having a pH greater than 7. In some such embodiments, the pH is in the range of 7 (but not including 7) to 11, or 8 to 10.

The composition also includes one or more film-forming polymers. In some embodiments, the film-forming polymer is a water-dispersible polymer. In some such embodiments, the film-forming polymer exists in the composition as a separate phase, which, for example, is dispersed in the aqueous medium. In some embodiments, the dispersed polymer can form a plurality of droplets that are dispersed in the aqueous medium. In some such embodiments, the droplets are dispersed in a manner so as to form an emulsion. In some instances, however, the composition may tend to phase separate into distinct layers, such as instances where the composition is left to sit for some length of time. Such phase-separated (or partially phase-separated) compositions are also within the scope of the disclosed compositions. In some embodiments, a small amount of the film-forming polymer may dissolve in the aqueous medium, although, in most embodiments, a predominant amount (e.g., at least 80% by weight, or at least 90% by weight, or at least 95% by weight, or at least 97% by weight, or at least 99% by weight, of the firm-forming polymer is not dissolved in the aqueous medium.

Any suitable firm-forming polymer can be used. Film-forming polymers that are dispersible in the aqueous medium are generally preferred. In some embodiments, the film-forming polymer is a natural latex. In some other embodiments, the film-forming polymer is a synthetic latex. Such synthetic latexes include, but are not limited to, acrylic polymers, polyvinyl acetate, polyvinyl chloride, styrene-butadiene rubber, other styrene polymers, acrylonitrile-butadiene rubber, epoxy resins, or any mixture thereof. In some embodiments, the firm-forming polymer is a mixture of a natural latex and one or more synthetic latex compositions. Certain polymers suitable for use in paint and coating applications are available commercially. A non-limiting example is RHOPLEX SG-30 acrylic resin (Dow Chemical Co., Midland, Mich., USA).

Any suitable amount of film-forming polymer can be used. The amount can vary depending on a variety of factors, including, but not limited to, the desired thickness of the composition, the desired end use of the composition, the properties of the film-forming polymer, the identity of other components in the composition, and the like. In some embodiments, the weight-to-weight ratio of film-forming polymer to water in the composition ranges from 1:2 to 10:1, or from 1:1 to 8:1, or from 2:1 to 6:1, or from 3:1 to 5:1. In embodiments where a co-solvent is used in addition to water, the foregoing ratios would apply to the total weight of solvent (water plus any co-solvents) and not exclusively to the water.

The compositions disclosed herein also include a coalescing aid, which includes one or more polyol esters of unsaturated fatty acids (according to any of the above embodiments).

As discussed in further detail below, in some embodiments, the one or more unsaturated fatty acids used to make the polyol esters thereof can be derived from a renewable source, such as from a natural oil. In some such embodiments, the one or more polyol esters of unsaturated fatty acids are derived from a process that includes metathesizing a natural oil or a natural oil derivative. Further details regarding such processes are provided below.

In some embodiments, the coalescing aid predominantly contains one or more polyol esters of unsaturated fatty acids according to any of the above embodiments. For example, in some embodiments, the one or more polyol esters of unsaturated fatty acids make up at least 50% by weight, or at least 60% by weight, or at least 70% by weight, or at least 80% by weight, or at least 90% by weight, or at least 95% by weight, or at least 97% by weight, or at least 99% by weight, of the coalescing aid. In some embodiments, the coalescing aid contains alkyl esters (e.g., methyl esters) of unsaturated $C_{12-16}$ carboxylic acids, including, but not limited to, 9-dodecenoic acid, 9,12-tridecadienoic acid, 11-tetradecanoic acid, 9-pentadecanoic acid, 9,12-pentadecadienoic acid. In some embodiments, the alkyl esters (e.g., methyl esters) of unsaturated $C_{12-16}$ carboxylic acids make up at least 50% by weight, or at least 60% by weight, or at least 70% by weight, or at least 80% by weight, or at least 90% by weight, or at least 95% by weight, or at least 97% by weight, or at least 99% by weight, of the coalescing aid.

The coalescing aid can also include some amount of esters (e.g., alkyl esters, such as methyl esters) of saturated carboxylic acids. Non-limiting examples include myristic acid, palmitic acid, and stearic acid. In embodiments where such saturated esters are present, they make up no more than 50% by weight, or no more than 40% by weight, or no more than 30% by weight, or no more than 20% by weight, or no more than 10% by weight.

In some embodiments, the coalescing aid can include one or more other compounds that can aid in the coalescing of the film-forming polymers. Suitable additional ingredients in the coalescing aid include, but are not limited to, 2,2,4-trimethyl-1,3-pentanediol isobutyrate, commercially available as TEXANOL (Eastman Chem. Co., Kingsport, Tenn., USA).

Any suitable amount of the coalescing aid can be used in the composition. The amount can vary depending on a variety of factors, including, but not limited to, the desired end use of the composition, the properties of the film-forming polymer, the identity of the components in the coalescing aid, and the like. In some embodiments, the weight-to-weight ratio of film-forming polymer to coalescing aid ranges from 5:1 to 200:1, or from 10:1 to 100:1, or from 15:1 to 60:1. In some embodiments, the weight-to-weight ratio of water to coalescing aid ranges from 4:1 to 100:1, or from 6:1 to 50:1, or from 8:1 to 25:1, or from 10:1 to 20:1. In embodiments where a co-solvent is used in addition to water, the foregoing ratios would apply to the total weight of solvent (water plus any co-solvents) and not exclusively to the water.

The composition can contain various other ingredients. In some embodiments, the composition can contain one or more colorants, such as pigments, dyes, and the like. Such colorants can be organic or inorganic, synthetic or natural. Non-limiting examples of suitable pigments include cadmium yellow, cadmium red, cadmium green, cadmium orange, carbon black (including vine black, lamp black), ivory black (bone char), chrome yellow, chrome green, cobalt violet, cobalt blue, cerulean blue, aureolin (cobalt yellow), Azurite, Han purple, Han blue, Egyptian blue, Malachite, Paris green, Phthalocyanine Blue BN, Phthalocyanine Green G, verdigris, viridian, sanguine, caput mortuum, oxide red, red ochre, Venetian red, Prussian blue, yellow ochre, raw sienna, burnt sienna, raw umber, burnt umber, lead white, cremnitz white, Naples yellow, red lead, vermilion titanium yellow, titanium beige, titanium white ($TiO_2$), titanium black, ultramarine, ultramarine green shade, zinc white, zinc ferrite, alizarin (synthesized or natural), alizarin crimson (synthesized or natural), gamboge, cochineal red, rose madder, indigo, Indian yellow, Tyrian purple, quinacridone, magenta, phthalo green, phthalo blue, pigment red 170, or any combinations thereof. In some embodiments, the composition at least includes titanium white (TiO$_2$).

Other ingredients can also be present in the composition. For example, in some embodiments, the composition includes one or more thickeners, one or more rheology modifiers, one or more surfactants, one or more defoamers, or any combination thereof. In some embodiments, the composition can include one or more biocide compounds.

Further, in some embodiments, the composition is an environmentally friendly composition, for example, that contains a low content of volatile organic components (VOCs). In some embodiments, the composition includes no more than 0.5 kg/L, or no more than 0.3 kg/L, or no more than 0.1 kg/L, of VOCs, as measured by Method 24 of the United States Environmental Protection Agency.

The above compositions can be put to a wide variety of different uses. For example, in some non-limiting examples, the compositions are suitable for use as paint or coating compositions. In some embodiments, the composition is an interior paint composition. In some other embodiments, the composition is an exterior paint composition.

Derivation from Renewable Sources

The polyol esters of unsaturated fatty acids employed in any of the aspects and embodiments disclosed herein can, in certain embodiments, be derived from renewable sources, such as various natural oils. Any suitable methods can be used to make these compounds from such renewable sources. Suitable methods include, but are not limited to, fermentation, conversion by bioorganisms, and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These polyol esters of unsaturated fatty acids may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters. In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, the polyol esters of unsaturated fatty acids may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, multiple metathesis reactions can also be employed. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The conditions for such metathesis reactions, and the reactor design, and suitable catalysts are as described above with reference to the metathesis of the olefin esters. That discussion is incorporated by reference as though fully set forth herein.

In the embodiments above, the natural oil (e.g., as a glyceride) is metathesized, followed by transesterification. In some other embodiments, transesterification can precede metathesis, such that the fatty acid esters subjected to metathesis are fatty acid esters of monohydric alcohols, such as methanol, ethanol, or isopropanol.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple metathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments were a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

Methods of Making Compositions

In certain aspects, the disclosure provides processes for making compositions according to any of the above embodiments.

The compositions disclosed herein can be made by any suitable process. In embodiments where the composition is a paint or coating composition, typical methods of making paint or coating compositions can be employed. For example, in some embodiments, certain materials (e.g., insoluble materials) can be ground together in a paste. The paste can then be dispersed into the aqueous medium with the polymer droplets suspended therein (e.g., as an emulsion).

Methods of Reducing the Minimum Film-Forming Temperature of a Polymer

In certain aspects, the disclosure provides methods of reducing the minimum film-forming temperature of a polymer.

In some embodiments, the method includes: providing a polymer composition, which comprises a film-forming polymer; and contacting the firm-forming polymer with a coalescing aid, which comprises one or more compounds unsaturated ester compounds according to any of the above embodiments. In some such embodiments, the method includes incorporating the film-forming polymer and the coalescing aid into a composition according to any of the above embodiments.

Methods of Painting or Coating a Surface

In certain aspects, the disclosure provides methods of painting or coating a surface. In some embodiments, the surface is an interior surface, such as an interior wall, an interior ceiling, interior woodwork, and the like.

In some embodiments, the method includes: providing a surface; and contacting the surface with a composition according to any of the above embodiments. In some such embodiments, the method includes painting the composition onto the surface, for example, with a suitable applicator, such as a brush, roller, sprayer, and the like.

EXAMPLES

Example 1: 2-Hydroxypropyl 9-dodecenoate 1,2-Propylene glycol (99%) (208 g, 2.73 mol) was sparged with nitrogen for 30 min and heated to 135 C.

Sodium methoxide (25% w/w in MeOH) (17.6 mL, 0.077 mol) was added and the solution stirred for 20 min. Next, methyl-9-dodecenoate (430 g, 2.03 mol) was added dropwise over 3 h and the reaction stirred for an additional 1.5 h with continuous removal of methanol into a dry ice cooled trap. A second charge of propylene glycol (99%) (114 g, 1.50 mol) was added and the reaction continued at 135 C for 1 h. The reaction was cooled to room temperature and the catalyst quenched to neutrality with phosphoric acid (85%) resulting in a sodium phosphate precipitate. The desired monoester product was purified by vacuum distillation to yield an odorless, colorless oil (445 g, 1.74 mol, 86%). GC-MS m/z calcd for $C_{15}H_{28}O_3(M)^+$: 256.2. found: 256.1. $^1$H NMR (400 MHz, CDCl$_3$): δ=0.96 (t, 3H), 1.20-1.30 (bm, 13H), 1.62 (m, 2H), 1.97 (m, 4H), 2.35 (m, 2H), 2.55 (bs, 1H), 3.91-4.12 (m, 2H), 5.32-5.46 (m, 2H). Density=0.894 g/mL. Percent volatile content (ASTM D2369)=32.9 g/L.

The 2-hydroxypropyl 9-dodecenoate was tested as a coalescent in a standard latex paint formulation, and, upon drying, yielded a paint having suitable film-forming and other performance-related properties.

Example 2: 3-Hydroxypropyl 9-dodecenoate

3-Hydroxypropyl 9-dodecenoate was made in a manner analogous to the method of Example 1, but using 1,3-propylene glycol instead of 1,2-propylene glycol. $^1$H NMR (CDCl$_3$): δ=0.88 (t, 3H, J=7.2 Hz), 1.23 (bm, 8H), 1.56 (m, 2H); 1.79 (m, 2H), 1.92 (m, 4H), 2.24 (t, 2H, J=7.6 Hz), 2.53 (bs, 1H), 3.61 (t, 2H, J=6.0 Hz), 4.15 (t, 2H, J=6.0 Hz), 5.30 (m, 2H).

The 3-hydroxypropyl 9-dodecenoate was tested as a coalescent in a standard latex paint formulation, and, upon drying, yielded a paint having suitable film-forming and other performance-related properties.

What is claimed is:

1. A compound of formula (I):

(I)

wherein:
R$^1$ is —CH$_2$—CH$_3$, —CH$_2$—CH=CH$_2$, or —CH$_2$—CH=CH—CH$_2$—CH$_3$; and R$^2$ is selected from the group consisting of:
—CH$_2$—CH$_2$—OH,
—CH$_2$—CH(OH)—CH$_3$,
—CH$_2$—CH(O—R$^4$)—CH$_3$,
—CH(—CH$_3$)—CH$_2$—OH,
—CH(—CH$_3$)—CH$_2$—OR$^5$,
—CH$_2$—CH$_2$—CH$_2$—OH,
—CH$_2$—CH$_2$—CH$_2$—O—R$^6$,
—CH$_2$—CH$_2$—CH$_2$—CH$_2$—OH,
—CH$_2$—CH(—CH$_3$)—CH$_2$—OH,
—CH$_2$—CH(—CH$_3$)—CH$_2$—OR$^8$,
—CH$_2$—C(—CH$_3$)$_2$—CH$_2$—OH,
—CH$_2$—C(—CH$_3$)$_2$—CH$_2$—OR$^9$,
—CH$_2$—CH$_2$—CH(—CH$_3$)—CH$_2$—CH$_2$—OH,
—CH$_2$—CH$_2$—CH(—CH$_3$)—CH$_2$—CH$_2$—OR$^{10}$,
—CH$_2$—CH(—OH)—CH$_2$—OH,
—CH$_2$—CH(—OH)—CH$_2$—OR$^{11}$,
—CH$_2$—CH(—OR$^{12}$)—CH$_2$—OH,
—CH$_2$—CH(—OR$^{12}$)—CH$_2$—OR$^{11}$,
—CH(—CH$_2$—OH)(—CH$_2$—OH),
—CH(—CH$_2$—OR$^{13}$)(—CH$_2$—OH),
—CH(—CH$_2$—OH)(—CH$_2$—OR$^{14}$),
—CH(—CH$_2$—OR$^{13}$)(—CH$_2$—OR$^{14}$); and
R$^3$, R$^4$, R$^5$, R$^6$, R$^8$, R$^9$, R$^{10}$, R$^{11}$, R$^{12}$, R$^{13}$, and R$^{14}$ are independently methyl or ethyl.

2. The compound of claim 1, wherein R$^1$ is —CH$_2$—CH$_3$.

3. The compound of claim 1, wherein R$^2$ is —CH$_2$—CH$_2$—OH.

4. The compound of claim 1, wherein R$^2$ is —CH$_2$—CH(OH)—CH$_3$.

5. The compound of claim 1, wherein R$^2$ is —CH$_2$—CH(O—R$^4$)—CH$_3$.

6. The compound of claim 5, wherein R$^4$ is methyl.

7. The compound of claim 5, wherein R$^4$ is ethyl.

8. The compound of claim 1, wherein R$^2$ is —CH(—CH$_3$)—CH$_2$—OH.

9. The compound of claim 1, wherein R$^2$ is —CH(—CH$_3$)—CH$_2$—OR$^5$.

10. The compound of claim 9, wherein R$^5$ is methyl.

11. The compound of claim 9, wherein R$^5$ is ethyl.

12. The compound of claim 1, wherein R$^2$ is —CH$_2$—CH$_2$—CH$_2$—OH.

13. The compound of claim 1, wherein R$^2$ is —CH$_2$—CH$_2$—CH$_2$—O—R$^6$.

14. The compound of claim 13, wherein R$^6$ is methyl.

15. The compound of claim 13, wherein R$^6$ is ethyl.

* * * * *